United States Patent [19]

Gelbard

[11] 4,338,300

[45] Jul. 6, 1982

[54] USE OF PURIFIED CLOSTRIDIAL COLLANGENASE IN THE TREATMENT OF PEYRONIE'S DISEASE

[75] Inventor: Martin K. Gelbard, Van Nuys, Calif.

[73] Assignee: The Regents Of The University Of California, Berkeley, Calif.

[21] Appl. No.: 231,731

[22] Filed: Feb. 5, 1981

[51] Int. Cl.³ .............................................. A61K 37/48
[52] U.S. Cl. ...................................................... 424/94
[58] Field of Search ............................................ 424/94

[56] References Cited

U.S. PATENT DOCUMENTS 4,174,389  11/1979  Cope ..................................... 424/94

OTHER PUBLICATIONS

Mailman–Chem. Abst. vol. 91 (1979) p. 52190k.
Kobayasi et al.–Chem. Abst. vol. 87 (1977) p. 165,284e.

*Primary Examiner*—Sam Rosen
*Attorney, Agent, or Firm*—Joseph E. Mueth

[57] ABSTRACT

The method of treating Peyronie's disease which comprises administering an effective amount of the enzyme collagenase directly into the plaques which form in the course of the disease.

7 Claims, No Drawings

USE OF PURIFIED CLOSTRIDIAL COLLANGENASE IN THE TREATMENT OF PEYRONIE'S DISEASE

BACKGROUND OF THE INVENTION

Peyronie's disease is characterized by a condition of unknown etiology wherein there is the development of plaques or masses of dense fibrous tissue in the fascia about the corpus cavernosum of the penis, resulting in deformation of the penis.

While recent advances have been made in the surgical treatment of Peyronie's disease, specific therapy for the problem continues to be unsatisfactory. It is universally acknowledged that there is no medical or local therapy that provides predictable and lasting benefits for the patient with this distressing problem.

According to the present invention, it has been found that collagenase can be injected into the plaque resulting in the softening with subsequent restoration of penile symmetry and function.

The specific collagenolytic properties of clostridial filtrates were first described in the 1940's. In 1964 it was found to consist of two distinct collagenases. These enzymes have been named Clostridiopeptidase A and Collagenase 2. Purified clostridial collagenase is available commercially in two forms, *Worthington Biochemical,* Freehold, N.J. 07728, a chromatographically purified preparation containing both collagenases with trace amounts of an unidentified protease contaminant, and a lyophylized chromatographically purified preparation of Clostridiopeptidase A. The bacterial collagenases act at many sites along the peptide chain, clipping short segments from each end. It is active over a wide pH range with an optimum around 7.4. Native collagen is its only substrate; globular, soluble, and other structural proteins are unaffected. Ensyme activity is high at 37° C. It is not subject to autodigestion and is not inhibited significantly in vivo. The purified preparation is quite stable with respect to time and its cost is reasonable. In experimental animals, toxic doses are far in excess of effective therapeutic doses.

The clinical use of bacterial collagenase has heretofore been limited to topical application for debridement of dermal ulcers and burn eschar. It has been proposed for use in treating prolapsed intervertebral discs, as a biochemical curretage of the herniated nucleosus pulposus. Although several animal studies have demonstrated some effect, it has not been used for this purpose in humans to date.

It is believed that the use of collogenase in the treatment of Peyronie's disease represents a significant advance in the art.

SUMMARY OF THE INVENTION

Briefly, the present invention comprehends the method of treating Peyronie's disease which comprises administering an effective amount of the enzyme collagenase directly into the plaques which form in the course of the disease.

The present invention also includes a novel aqueous parenteral solution containing an effective amount, on the order of 0.1% to about 2% by weight, of collagenase for injection into the plaques which form in Peyronie's disease.

It is an object of this invention to provide a novel treatment for Peyronie's disease.

More particularly, it is an object of this invention to provide a new, non-surgical treatment which restores the form and function of the penis.

It is also an object of this invention to provide a novel parenteral solution useful for the treatment of Peyronie's disease.

These and other objects and advantages of this invention will be apparent from the more detailed description which follows.

DESCRIPTION OF THE PREFERRED EMBODIMENTS

All collagenase used in thus study was the chromatographically purified preparation containing both collagenases described above (code CLSPA Worthington Labs). It was stores at $-20°$ C. in lyophylized form until the day it was used, at which time it was suspended in 0.05 M potassium phosphate, 0.00036 M calcium chloride buffer at pH 7.4.

The estimated dose required to an effect on Peyronie's plaques in vivo is in the range of 100 to 400 units as a 0.5% solution. The acute intravenous $LD_{50}$ in rats has been shown to be $1272 \pm 156$ units/kg for purified clostridial collagenase. Although extrapolation of these figures to humans is probably inaccurate, it is useful for comparison. For the 70 kg man, an intravenous $LD_{50}$ of 89,040 units is obtained, which is in excess of the average effective dose for Peyronie's plaques by a factor of 356. It has also been reported that there were no adverse changes in red cell, white cell, or platelet counts in rats receiving 100 times the effective dose for discolysis.

The administration of collagenase has immunologic consequences. Braun, W. P. H.: Contact Allergy to Collagenase Mixture (Iruxol). Cont. Derm. 1:241 (1975). With injections repeated after the development of antibody titers there would be a risk of anaphylaxis or other less serious hypersensitivity reactions. Also the presence of specific antibodies inhibits the enzyme. Mandl, I.: Collagenases and Elastases in Advances in Enzymology 23:163, F. F. Nord, Editor, Intersciences, N.Y. (1961). However, if the time required to mount an antibody response is considered it is apparent that multiple injections could be given over a short (4 to 6 day) period. Repeated immunization prior to the development of high antibody titers does not produce eventual titers significantly different from those expected with a single immunization. Handbook of Experimental Immunology, Weig, D. M. Editor, Blackwell, Oxford, (1976). The classic amnestic response with amplified antibody production following a booster occurs only if the booster is given in the presence of substantial antibody titers.

The following Examples are presented solely to illustrate the invention.

EXAMPLE I

Samples of Peyronie's plaques were obtained from three different patients. In addition, several segments of normal tunica albuginea were obtained from patients without peryronie's disease who were operated on for placement of penile prostheses. The tissue was quick frozen with dry ice and stored at $-20°$ C. for approximately ten days.

The frozen specimens were dessicated and dry weights recorded. The activity of collagenase was then determined on each specimen. Each tissue fragment was incubated at 37° C. for 48 hours in 5 ml of a 0.02% solution of collagenase in buffer. Mild magnetic stirring was continued throughout the incubation. One-tenth of a ml of the supernatant was removed from each incubation tube at hourly intervals up to five hours, then again at 24 and 48 hours. Collagenase action was terminated in these 0.1 ml samples by addition of 3 drops of glacial acetic acid followed by lyophylization. The residue obtained was stored at −20° C. At 48 hours of incubation the plaque fragments were removed, washed in distilled water, dessicated, and weighed.

The extent of enzymatic collagenolysis over time was then assayed by determination of the free $\alpha$-amino group content of each lyophylized aliquot by the colorimetric ninhydrin method. The dried aliquots were suspended in 0.2 ml of distilled water, and the pH checked to insure it was about 5. Two ml of ninhydrin reagent were added, and the mixture heated over steam for 20 minutes. After cooling, all samples were diluted with 5 ml of 50% ethanol. The absorbance was read at 600 nm in a Zeiss PMQII uv/vis spectrophotometer. High optical density samples were re-diluted and the readings corrected for the dilution factors. All optical density readings were then normalized for pre-digestion tissue dry weights.

Two other determinations were made. In one, plaque tissue was incubated in a 0.02% collagenase solution in 50% fresh human serum and buffer. The second was a control in which three pieces of plaque tissue and one piece of tunica albuginea in buffer without collagenase and subjected to the mechanical effects of magnetic stirring alone.

Although plaque and tunica tissue was incubated for 48 hours, ninhydrin readings demonstrated that most free $\alpha$-amino groups were released in the first 24 hours (FIGS. 1 and 2). Substantial reductions in tissue dry weights were recorded and failed to demonstrate any selectivity of the enzyme for plaque collagen over tunica albuginea collagen. Of the three tunica specimens the maximum decrease in dry weight observed following digestion was 99%. For the plaque fragments incubated in collagenase and buffer the maximum loss of dry weight was greater than 99%, with a mean decrease of 88.6% for the three specimens. These figures are significant when compared to controls, tissue subjected to incubation and mechanical stirring without collagenase. The maximum reduction in dry weight under these conditions was 12% with a mean of 9.3% for the three plaque segments. The single tunica albuginea control showed a 17% reduction in dry weight. The plaque fragment incubated with human serum underwent a 51% reduction in dry weight but could not be plotted on the curve because of extremely high background ninhydrin readings.

The increase in free $\alpha$-amino groups that parallels tissue weight loss implies the dissolution represents enzymatic collagen cleavage. Moreover, since the specificity of purified collagenase has been demonstrated, the above measurements provide an estimate of the biochemical composition of the plaques. It appears that they are largely collagen.

EXAMPLE II

Fresh human pericardium was obtained at autopsy. After complete defatting it was frozen flat between layers of cellophane and stored at −20° C. The tissue was thawed by soaking in the above buffer at 37° C. "Intradermal" injections of differing strengths of enzymes were made in the center of each piece. Six concentrations were used: 10 U, 30 U, 60 U, 100 U, 200 U, and 400 Units each in 0.1 ml of buffer. A bleb was raised and the excess solution blotted off. Paper markers were placed to identify the injection sites. These tissue sheets were placed on filter paper in glass petri dishes and incubated 24 hours at 37° C. They were then transferred to 10% neutral formalin. Histologic sections were taken through the injection site, then stained with hemotoxylin/eosin and Van Gieson's (a stain for follagen). Pericardial thickness at the center of the sections and at the edges was determined as the mean of 4 measurements made in each area using a microscope with a micrometer ocular.

In the piece of pericardium injected with 400 units of collagenase a grossly visible zone of clearing was noted in the fixed tissue centering around the injection site. Its diameter was not greater than that of the bleb raised at the time of injection. Lesser doses exhibited microscopic evidence of thinning. The radius of the thinned area did not change with dose to any extent, remaining approximately the size of the initial injection bleb.

The percent of thinning derived from the center and edge measurements of each piece was then plotted against dosage. It demonstrated that in a uniform substrate increasing the dose tended to increase the amount of lysis. The lack of any increase in the radius of lysis with increasing dosage illustrates that the enzyme does not spread readily through tissue in vitro. It appears to exert its effects while confined to the region of injection.

EXAMPLE III

Several simple experiments were undertaken in vivo. In the first, dorsal interscapular dog skin was injected intradermally with several strengths of sterile collagenase solution. These were 60 U, 100 U, 200 U, and 400 Units in 0.1 ml, respectively. Injection sites were inspected at 30 minutes, 24 hours, then daily for a week. A biopsy of the 400 U injection site was taken at 24 hours. Dorsal rabbit skin was injected subcutaneously with the same dosages and inspected on the same schedule.

The right achilles tendon sheath was exposed surgically in an anesthetized dog. It was injected in each of 3 sites spaced 1 cm apart with 0.2 ml of a sterile 0.18% collagenase solution (120 units). Fine silk sutures were placed to mark the injection sites and the wound closed. At 24 hours, 3 days, and 1 week, operations were done to remove one of the marked sites at a time. At one week the animal was sacrificed and a segment of the contralateral tendon obtained as a control. All tissue was sectioned after fixation and stained with hemotoxylin/eosin and Van Gieson's stain.

In an anesthetized rat the left ferormal neurovascular structures were exposed surgically. Two-tenths of a ml of a sterile solution containing 600 U of collagenase in buffer was infiltrated in the adventitial tissues surrounding them and the wound closed. Twenty-four hours later the rat was sacrificed and the block of tissue containing this area removed. Corresponding tissue from the contralateral side was removed as a control then fixed, sectioned and stained as described above.

An interesting comparison emerged from the two skin injection trials. Whereas the intradermal injection of 400 units into tick dorsal dog skin resulted in ulceration within 24 hours, the same dose injected subcutaneously in rabbits produced no visible change in their considerably thinner skin. The biopsy taken from the ulcer produced by intradermal injection showed dermal collagenolysis and a polymorphonuclear leucocyte infiltrate.

Two features were observed in the tendon injection when compared to the control: Collagenolysis and inflammatory response. The cellular inflammatory response, which was present principally in the one week section, was likely due in part to the fact that three operations were done on the same tendon. The collagenolysis increased progressively, with a greater degree apparent at 7 days than at 3 days.

When the rat femoral canal was re-opened following collagenase injection a moderate hematoma was noted. This appeared to have come from small vessels, as no active bleeding was seen at the time the tissue was harvested. The microscopic sections confirmed that there was no damage to arterioles and arteries containing smooth muscle. Some small veins appeared to have ruptured. Although there was dissolution of the fibrous perineurium, no change in the nerve fibers was seen on the injected side when compared with the control.

EXAMPLE IV

Three segments of human corpora cavernosa from the penis were excised at autopsy within four hours of death. The specimens were divided and one-half reserved as a control. The other half was soaked in buffer for one hour to normalize tissue pH. It was then injected in the dorsal midline with 0.2 ml of a 0.5% collagenase solution (400 U). Control and injected tissue was placed on filter paper in glass petri dishes and incubated at 37° C. for 24 hours. The tissue was fixed and sectioned. It was stained with hemotoxylin/eosin, Van Gieson's stain, and elastic Van Gieson's stain.

Definite collagenolysis occurred in the injected corpora within a 2 mm radius of the injection site. This was apparent in the sections stained with Van Gieson's technique and ranged from complete disappearance of collagen fiber bundles to vacuolization and loss of their characteristic staining properties. The enzyme's specificity for collagen was shown in the sections stained for elastin fibers. There was excellent preservation of elastic elements in areas where collagen had been completely dissolved.

EXAMPLE V

A segment of freshly obtained Peyronie's plaque was divided into two equal parts. The matching faces of each piece were marked with mercurochrome. A volume of 0.1 ml of a 1.0% collagenase solution (400 U) was injected into one piece. Both pieces were then incubated in the same manner as the corpora. At 24 hours they were fixed in formalin and sectioned parallel to the marked faces. Slides were stained with hemotoxylin/eosin and Van Gieson's stain.

A gross zone of lysis can be seen dorsally in a complete penile cross section. A higher magnification of a similar injected speciment shows there has been substantial loss of tunica albuginea collagen in the dorsal midline. At higher power the more superficially located vessels and nerves showed no histologic evidence of injury or digestion.

The injected Peyronie's plaque fragment underwent considerable reduction in overall size. Microscopically the treated plaque showed widespread fraying and dispersal of collagen bundles compared to the dense compact collagen seen in the untreated tissue.

While collagenase causes extensive dissolution in vitro of the tissue comprising Peyronie's plaques as well as the surrounding normal collagenous tissue, there are factors which overcome this lack of selectivity and permit its use in the treatment of Peyronie's disease.

Although the pericardial lysis assay cannot be interpreted quantitatively, it shows qualitatively that the extent of anzyme-induced collagenolysis is related to the dosage used. This experiment also showed that very little diffusion and spreading occur from the site of initial enzyme deposition. This anatomical confinement of digestion is related to the mucopolysaccharide "ground substance" which embeds the collagen in connective tissue but is not subject to the action of collagenase. Anderson, J. C.: Clycoproteins of the Connective Tissue Matrix. Int. Rev. Conn. Tiss. Res. 7:251 (1976).

The specificity of collagenase for its substrate has other desirable consequences. Elastic tissue is preserved, a feature which may be particularly important in treating Peyronie's disease. Fragmentation of elastic fibers has been observed in this condition, Mukherjee, A., Khan, K. P., Ganguly, N. C., Dey, T. K.: Plastic Induration of Penis: Peyronies Disease—A Histopathological Study, Indian J. Path/Micro. 21:197 (1978), which would make salvage of existing elastic elements mandatory for preservation of normal tissue mechanical properties. Vascular smooth muscle is not digested by this enzyme which protects all vessels except small venules. Collagen forms the bulk of their walls up to 0.2 mm, where a well developed circular coat of smooth muscle begins to appear. Although nerve fiber bundles are sheathed in a collagenous perineurium, the axons themselves are wrapped in myelin, a lipid not digested by collagenase. Rat fermoral nerves treated in vivo with high doses of collagenase showed excellent histologic preservation of fibers. Indeed collagenase has been used to selectively remove the connective tissue which surrounds nerves, isolating them for histologic study. Mandl, I., (Editor): Collagenase, Gordon and Breach, New York, N.Y. (1972). Garvin and Jennings studied the physiologic effects of chymopapain on animal nerves in vivo. Garvin, P. J., Jennings, R. B., Smith, L., Gesler, R. M.: Chymopapain: A Pharmacologic and Toxicologic Evaluation in Experimental Animals. Clinical Orthopedics and Related Research 41:204 (1965). Although chymopapain is a protease with a wide range of substrates they found it caused no change in threshold voltages for muscle twitch or sensory ending response. The abundant data on collagenase use for dispersion in cell culture techniques has shown it is not cytotoxic, and does not harm cell membranes. Mandyl, I., (Editor): Collagenase, Gordon and Breach, New York, N.Y. (1972).

Earlier reports indicated that normal human serum contains anticollagenases although in extremely weak titers. Mandl, I.: Collagenases and Elastases in Advances in Enzymology 23:163, F. F. Nord, Editor, Intersciences, N.Y. (1961). Collagenase from Cl. Histolyticum was especially resistant to these inhibitors. The plaque tissue incubated with fresh human serum underwent a considerable decrease in dry weight when compared to controls. There is not sufficient data for valid comparison of this group against plaques incubated without serum. A marked dissolution of dermis in vivo was observed over a short time span. Since dermis is over 70% collagen, Crisp, J. C. D.: Properties of Skin and Tendon in Biomechanics; Fung, Y. C., Perrone, N., Anliker, M., Editors, Prentice-Hall, Englewood Cliffs, N.J. (1972), it appears that the enzyme displayed substantial action on its substrate in vivo. Fortunately, dermal injury was not seen with subcutaneous injection.

The injected autopsy tissue demonstrated how localized collagenolysis can be produced. The size of the area dissolved in this model may not be completely equivalent to the effect of the same dose in vivo, however. Studies of dog tendons in vivo showed that resorption of collagen continues to occur from the injection site after 24 hours. The amount of collagen "dissolved" (that which lost its tinctorial qualities in Van Gieson's stain) in the autopsy material represents the collagen that had undergone extensive enzymatic cleavage. As implied by the tendon studies, adjacent collagen undergoes denaturation to a lesser degree and is probably resorbed as the cellular inflammatory reaction sets in. To produce in humans the amount of lysis seen in the autopsy tissue injected with 400 units, it is estimated only 200 to 300 units would be required. Two factors tend to limit unpredictable continuation of collagenolysis. As noted previously, the enzyme does not spread well. In addition, the duration of enzymatic action is limited to approximately 24 hours.

Having fully described the invention, it is intended that it be limited only by the lawful scope of the appended claims.

I claim:

1. The method of treating Peyronie's disease in mammals which comprises administering an effective amount of the enzyme collagenase directly into the plaques which form in the course of the disease.

2. The method of treating Peyronie's disease in humans which comprises administering an effective amount of the enzyme collagenase directly into the plaques which form in the course of the disease.

3. The method of claim 2 wherein the collagenase is a mixture of Clostridiopeptidase A and Collagenase 2.

4. The method of claim 2 wherein the collagenase is lyophylized Clostridiopeptidase A.

5. The method of claim 2 wherein the collagenase is administered as a 0.5% buffered solution.

6. The method of claim 5 wherein the collagenase is administered in the range of 100 to 400 units.

7. The method of claim 5 wherein the collagenase is administered intralesionally.

* * * * *